United States Patent
Matsuura

(10) Patent No.: US 9,588,009 B2
(45) Date of Patent: Mar. 7, 2017

(54) ULTRASONIC FATIGUE TESTING MACHINE AND ULTRASONIC FATIGUE TESTING METHOD

(71) Applicant: SHIMADZU CORPORATION, Kyoto (JP)

(72) Inventor: Tohru Matsuura, Kyoto (JP)

(73) Assignee: SHIMADZU CORPORATION, Kyoto-shi (JP)

( * ) Notice: Subject to any disclaimer, the term of this patent is extended or adjusted under 35 U.S.C. 154(b) by 192 days.

(21) Appl. No.: 14/430,291

(22) PCT Filed: Dec. 7, 2012

(86) PCT No.: PCT/JP2012/081787
§ 371 (c)(1),
(2) Date: Mar. 23, 2015

(87) PCT Pub. No.: WO2014/087538
PCT Pub. Date: Jun. 12, 2014

(65) Prior Publication Data
US 2015/0226634 A1    Aug. 13, 2015

(51) Int. Cl.
*G01N 29/04*    (2006.01)
*G01M 7/02*    (2006.01)

(52) U.S. Cl.
CPC .......... *G01M 7/022* (2013.01); *G01N 29/04* (2013.01); *G01N 2203/0008* (2013.01);
(Continued)

(58) Field of Classification Search
CPC .......... G01N 29/04; G01N 2203/0008; G01N 2291/0258; G01N 2291/0289;
(Continued)

(56) References Cited

U.S. PATENT DOCUMENTS 3,529,465 A * 9/1970 Eisenmenger .......... G01N 3/38
73/577
2015/0053017 A1* 2/2015 Khonsari ................. G01N 3/34
73/801
(Continued)

FOREIGN PATENT DOCUMENTS

JP    62-128350 U    8/1987
JP    2007-17288 A    1/2007
(Continued)

OTHER PUBLICATIONS

Takanashi et al., "Estimation of self-heating quantity and temperature distribution in ultrasonic fatigue test specimen", The Japan Society of Mechanical Engineers M&M Zairyo Rikigaku Conference, vol. 2010, Oct. 8, 2010, p. ROMBUNNO.1112 (4 pages).
(Continued)

*Primary Examiner* — J M Saint Surin
(74) *Attorney, Agent, or Firm* — Westerman, Hattori, Daniels & Adrian, LLP

(57) ABSTRACT

This ultrasonic fatigue testing machine is one that resonates a test piece by an ultrasonic wave to perform a fatigue test, and configured to include an ultrasonic wave generation part 10, a displacement measurement part 20, and a control part 30 that controls the overall operation of the ultrasonic fatigue testing machine. The control part 30 is configured to have a computer that includes storage devices capable of store programs and various types of data, such as an RAM and an ROM, and an arithmetic unit such as a CPU, and includes an internal temperature estimation part 31, an allowable range setting part 32, and a determination part 33 as a main functional configuration.

4 Claims, 3 Drawing Sheets

(52) U.S. Cl.
CPC ............... *G01N 2291/0234* (2013.01); *G01N 2291/0258* (2013.01); *G01N 2291/0289* (2013.01); *G01N 2291/02827* (2013.01)

(58) Field of Classification Search
CPC  G01N 2291/0234; G01N 2291/02827; G01M 7/022
USPC .......................................................... 73/577
See application file for complete search history.

(56) References Cited

U.S. PATENT DOCUMENTS

| | | | |
|---|---|---|---|
| 2015/0233850 A1* | 8/2015 | Seok ...................... | G01N 25/72 374/5 |
| 2016/0061688 A1* | 3/2016 | Van Wittenberghe ..... | G01M 3/2853 73/577 |

FOREIGN PATENT DOCUMENTS

| | | | | |
|---|---|---|---|---|
| JP | 2010-271248 A | | 12/2010 | |
| JP | 2013221872 | * | 10/2013 | ............... G01N 3/32 |
| JP | 2015210094 | * | 11/2015 | ............. G01N 29/04 |
| WO | WO2016043514 | * | 3/2016 | ............. G01N 21/64 |

OTHER PUBLICATIONS

International Search Report dated Feb. 12, 2013 issued in corresponding application No. PCT/JP2012/081787.

\* cited by examiner

ULTRASONIC FATIGUE TESTING MACHINE AND ULTRASONIC FATIGUE TESTING METHOD

TECHNICAL FIELD

The present invention relates to an ultrasonic fatigue testing machine and ultrasonic fatigue testing method that resonate a test piece by an ultrasonic wave to perform a fatigue test.

BACKGROUND ART

There has been conventionally known an ultrasonic fatigue test that evaluates a fatigue life of a metallic material or the like by using an ultrasonic wave to oscillate a test piece. In such an ultrasonic fatigue test, stress is repetitively loaded on a test piece by resonating the test piece with, for example, sine wave oscillation at 20 kHz.

On the other hand, in the ultrasonic fatigue test, the high-frequency repetitive load is applied to the test piece, and therefore a rise in temperature of the test piece caused by the internal heat generation of a material becomes problematic. For this reason, there has been proposed an ultrasonic fatigue testing machine that measures temperature near a test piece during a test, and when the temperature reaches a predetermined temperature or more, sprays liquid nitrogen to cool the test piece (see Patent Literature 1).

Also, there has been proposed an ultrasonic fatigue testing machine that in order to suppress the internal heat generation of a test piece, periodically repeats excitation, which applies ultrasonic oscillation to the test piece, and a pause, i.e., performs so-called intermittent operation (see Patent Literature 2).

CITATION LIST

Patent Literature

[Patent Literature 1]
  Japanese Unexamined Utility Model Publication JP-U62-128350
[Patent Literature 2]
  Japanese Unexamined Patent Publication JP-A2007-17288

SUMMARY OF INVENTION

Technical Problem

Meanwhile, in the case of performing intermittent operation in an ultrasonic fatigue test, it is necessary to appropriately adjust an excitation time for loading ultrasonic oscillation on a test piece and a pause time for pausing excitation to cool the test piece so as to make it possible to apply the oscillation to the test piece the same number of times in a short period of time while keeping a rise in temperature of the test piece lower than an allowable range suitable for a material.

On the other hand, the amount of heat generation inside a test piece caused by ultrasonic oscillation is varied by a difference in stress load for oscillating the test piece. Also, the amount of heat generation inside a test piece is varied by a difference in material of the test piece, surface treatment, or the like even in the case of applying the same stress load to the test piece. Further, in the case of combining intermittent operation and cooling by spraying cooling air in order to suppress a rise in temperature of a test piece, a cooling speed of the test piece is varied by a spraying direction of the cooling air toward the test piece or the temperature of the cooling air.

The ultrasonic fatigue testing machine described in Patent Literature 1 measures the temperature of the test piece; however, regarding the temperature of the test piece, the temperature (surface temperature) near the test piece varied by heat emitted from the surface of the test piece is measured, but temperature inside the test piece is not measured. For this reason, even in the case where the surface temperature of the test piece is low, the temperature inside the test piece may still be in a high state.

Further, in the test by this sort of conventional ultrasonic fatigue testing machine, intermittent operation is performed according to excitation and pause periods determined through trial and error by a tester; however, work to obtain optimum excitation and pause timings for the intermittent operation is time-consuming work for the tester. In addition, the excitation and pause timings that the tester determined while consuming time may not be necessarily optimum timings. The optimum timings here refer to repetitive excitation and pause timings that make a test time shortest in the case of applying oscillation to a test piece the same number of times while keeping the amount of heat generation of the test piece lower than a temperature rise allowable in the fatigue test. In the case of failing to apply excitation and a pause to a test piece at such optimum timings, the fatigue test itself may result in failure. As described, for this sort of conventional ultrasonic fatigue testing machine, it is difficult to preliminarily appropriately set excitation and pause timings for intermittent operation in consideration of temperature inside a test piece during the test, which is varied depending on the type of the test piece, test details, or the like.

The present invention is made in order to solve the above problem, and intends to provide an ultrasonic fatigue testing machine that makes it possible to appropriately adjust an excitation time and a pause time in intermittent operation during a test.

Solution to Problem

An invention according to a first aspect of the present invention is an ultrasonic fatigue testing machine including: an oscillator that outputs an electrical signal adapted to generate a high frequency wave; an ultrasonic transducer that receives the electrical signal from the oscillator to oscillate; a horn of which a fore end is attached with a test piece, which amplifies ultrasonic oscillation from the ultrasonic transducer to transmit the amplified ultrasonic oscillation to the test piece; and a displacement meter that is arranged in a position away, by a predetermined distance, from an end surface of a free end of the test piece on a side opposite to an end part fixed to the horn, and measures a distance to the end surface of the test piece, and performing a fatigue test in an intermittent operation mode that repeats excitation applied to the test piece and a pause, and the ultrasonic fatigue testing machine includes a control part that has an internal temperature estimation part that from a variation in the distance from the displacement meter to the end surface of the test piece measured by the displacement meter, estimates internal temperature of the test piece due to internal heat generation of a material caused by the ultrasonic oscillation, and on the basis of the internal temperature of the test piece estimated by the internal temperature estimation part, controls a start and a stop of the signal output from the oscillator.

Regarding an invention according to a second aspect of the present invention, in the invention according to the first aspect, the internal temperature estimation part estimates the internal temperature of the test piece with use of a linear expansion coefficient of the material of the test piece.

Regarding an invention according to a third aspect of the present invention, in the invention according to the first aspect, the control part has: an allowable range setting part that sets a maximum allowable amount and a minimum allowable amount of the variation corresponding to a rise in the internal temperature of the test piece, which is allowable during the test; and a determination part that when the test piece is excited, determines whether or not the variation is larger than the maximum allowable amount, and when the excitation applied to the test piece is paused, determines whether or not the variation is smaller than the minimum allowable amount, and in the case where when the test piece is excited, the determination part determines that the variation is larger than the maximum allowable amount, the control part pauses the signal output from the oscillator, whereas in the case where when the excitation applied to the test piece is paused, the determination part determines that the variation is smaller than the minimum allowable amount, the control part starts the signal output from the oscillator.

An invention according to a fourth aspect of the present invention is an ultrasonic fatigue testing method that performs a fatigue test in an intermittent operation mode that repeats excitation applied to a test piece and a pause in an ultrasonic fatigue testing machine including: an oscillator that outputs an electrical signal adapted to generate a high frequency wave; an ultrasonic transducer that receives the electrical signal from the oscillator to oscillate; a horn of which a fore end is attached with a test piece, which amplifies ultrasonic oscillation from the ultrasonic transducer to transmit the amplified ultrasonic oscillation to the test piece; and a displacement meter that is arranged in a position away, by a predetermined distance, from an end surface of a free end of the test piece on a side opposite to an end part fixed to the horn, and measures a distance to the end surface of the test piece, and the ultrasonic fatigue testing method includes: an internal temperature estimation step of, from a variation in the distance from the displacement meter to the end surface of the test piece measured by the displacement meter, estimating internal temperature of the test piece due to internal heat generation of a material caused by the ultrasonic oscillation; an allowable range step of setting a maximum allowable amount and a minimum allowable amount of the variation corresponding to a rise in the internal temperature of the test piece, which is allowable during the test; and a determination step of, when the test piece is excited, determining whether or not the variation is larger than the maximum allowable amount, and when the excitation applied to the test piece is paused, determining whether or not the variation is smaller than the minimum allowable amount, and in the case where when the test piece is excited, it is determined in the determination step that the variation is larger than the maximum allowable amount, the ultrasonic fatigue testing method pauses the signal output from the oscillator, whereas in the case where when the excitation applied to the test piece is paused, it is determined in the determination step that the variation is smaller than the minimum allowable amount, the ultrasonic fatigue testing method starts the signal output from the oscillator.

Advantageous Effects of Invention

According to the inventions described in the first aspect and the second aspect, since the amount of heat generation inside the test piece is estimated from the variation in distance from the displacement meter to the end surface of the test piece corresponding to a displacement amount of the test piece during the test, an excitation time and a pause time in the intermittent operation can be appropriately adjusted during the test depending on the internal temperature of the test piece. Accordingly, the ultrasonic fatigue test can be appropriately performed.

According to the inventions described in the third aspect and the fourth aspect, since the allowable range setting part (allowable range setting step) that sets the maximum allowable amount and the minimum allowable amount of the displacement amount of the test piece corresponding to the rise in internal temperature of the test piece, and the determination part (determination step) that when the test piece is excited, determines whether or not the displacement amount is larger than the maximum allowable amount, and when the excitation applied to the test piece is paused, determines whether or not the displacement amount is smaller than the minimum allowable amount are provided, heat generation of the test piece during the test can be controlled so as to fall within the allowable range in the fatigue test, and therefore the fatigue test can be more appropriately performed.

DESCRIPTION OF EMBODIMENTS

Figure 1:
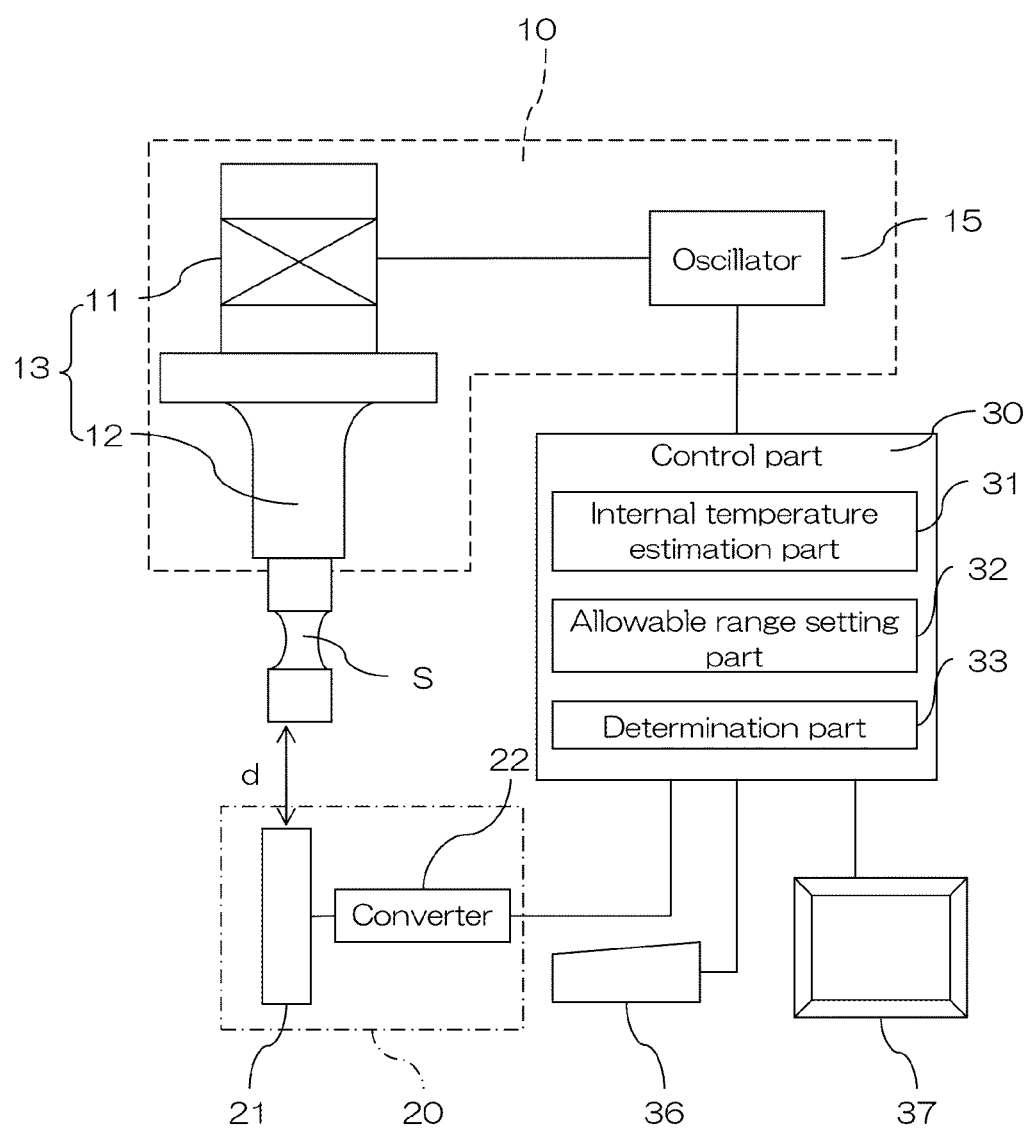
FIG. 1 is a schematic diagram illustrating a main configuration of an ultrasonic fatigue testing machine of this invention.

An embodiment of the present invention is described below on the basis of the drawings. FIG. 1 is a schematic diagram illustrating a main configuration of an ultrasonic fatigue testing machine of this invention.

The ultrasonic fatigue testing machine is one that resonates a test piece S by an ultrasonic wave to perform a fatigue test, and configured to include an ultrasonic wave generation part 10, a displacement measurement part 20, and a control part 30 that controls the overall operation of the ultrasonic fatigue testing machine.

The ultrasonic wave generation part 10 has: an oscillation part 13 that includes an ultrasonic transducer 11 and a horn 12; and an oscillator 15 that prepares a signal for oscillating the ultrasonic transducer 11. The oscillator 15 prepares the electrical signal on the basis of a test frequency set in the control part 30. The ultrasonic transducer is driven by the electrical signal outputted from the oscillator 15, and generates ultrasonic oscillation. The ultrasonic oscillation is amplified by the horn 12, and transmitted to a test piece S attached to the fore end of the horn 12. That is, by oscillating the ultrasonic transducer 11, repetitive stress is loaded on the test piece S fixed to the fore end of the horn 12.

The displacement measurement part 20 has: a displacement meter 21 that measures the displacement of the test piece S connected to the fore end of the horn 12; and a converter 22 that converts a detection value of the displacement meter 21 from an analog signal to a digital signal, and transmits the digital signal to the control part 30. The displacement meter 21 is arranged in a position away, by a predetermined distance, from the end surface of a free end side of the test piece S, which is the side opposite to the side where the test piece S is fixed to the horn 12. The displacement meter 21 is an eddy current displacement meter that measures a distance to the end surface of the test piece S in a contactless manner. Note that the distance between the displacement meter 21 and the end surface of the test piece S is herein referred to as an end surface gap d. Also, a value of the end surface gap d measured by the displacement meter 21 is inputted to the control part 30 through the converter 22. In addition, a variation in end surface gap d is also equivalent to a displacement amount of the test piece S.

The control part 30 is configured to have a computer that includes storage devices capable of store programs and various types of data, such as a RAM and a ROM, and an arithmetic unit such as a CPU, and functions as control means of this invention. The control part 30 is connected with a display part 37 and an input part 36. The input part 36 receives operations by an operator, such as changes in test conditions. The display part 37 displays the test conditions, the displacement of the test piece S during the test, and the like. Also, the control part 30 includes an internal temperature estimation part 31, an allowable range setting part 32, and a determination part 33 as a main functional configuration.

The internal temperature estimation part 31 estimates a variation in internal temperature of the test piece S from a displacement amount of the test piece S. To estimate the variation in internal temperature of the test piece S, a linear expansion coefficient already known for each material is utilized. The linear expansion coefficient refers to the rate of change of elongation caused by a temperature rise of 1° C. per unit length. Accordingly, from the variation in end surface gap d measured by the displacement meter 21, the variation in internal temperature of the test piece S can be estimated using the length of the test piece S and the linear expansion coefficient. In addition, a value of the length of the test piece S used for calculation to estimate the variation in internal temperature of the test piece S is determined depending on the shape of the test piece S or the length of a region on which stress is concentrated. Further, the variation in temperature inside the test piece estimated by the calculation using the variation in end surface gap d corresponding to the displacement amount of the test piece S, and the linear expansion coefficient is displayed in the display part 37 as needed.

The allowable range setting part 32 sets the maximum allowable amount of the variation in end surface gap d, which serves as a (pause) reference for temporarily stopping the ultrasonic excitation during the test, and the minimum allowable amount of the variation in end surface gap d, which serves as a reference for restarting the excitation after the pause of the ultrasonic excitation.

Figure 2:
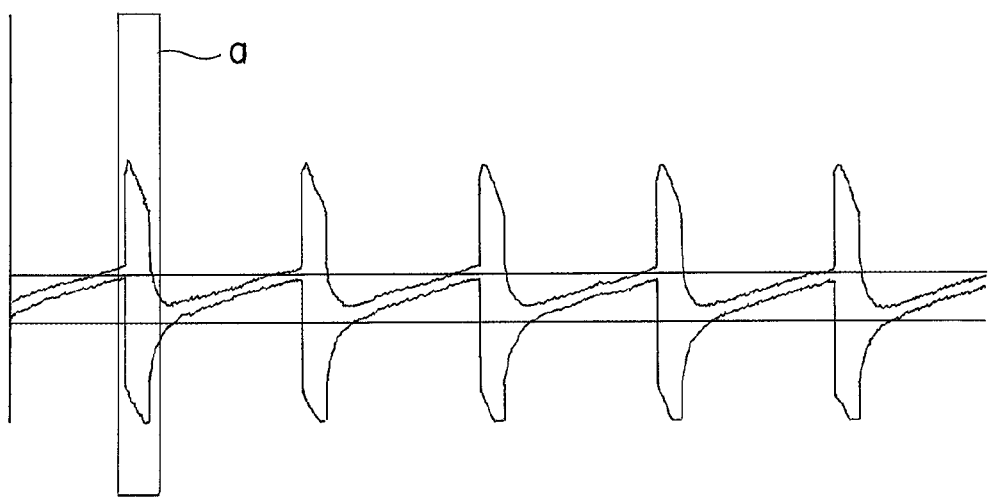
FIG. 2 is a graph illustrating a measurement result of an end surface gap d during a fatigue test in an intermittent operation mode.
Figure 3:
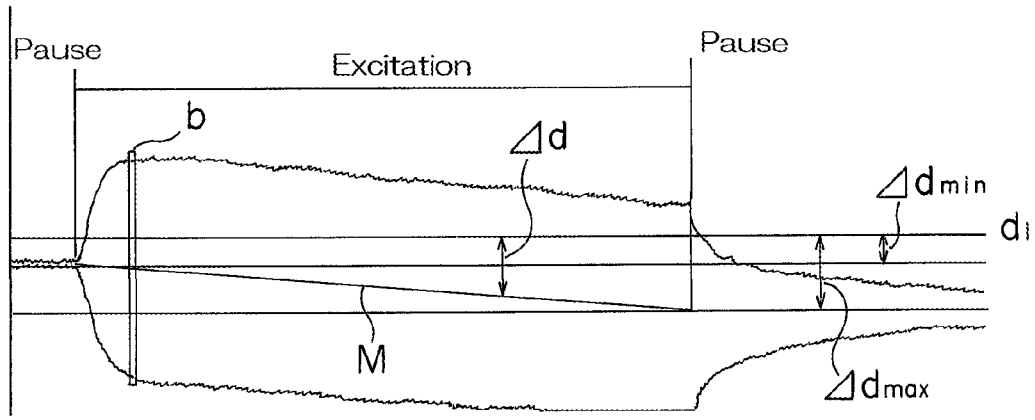
FIG. 3 is an enlarged view of a rectangular part a in FIG. 2.
Figure 4:
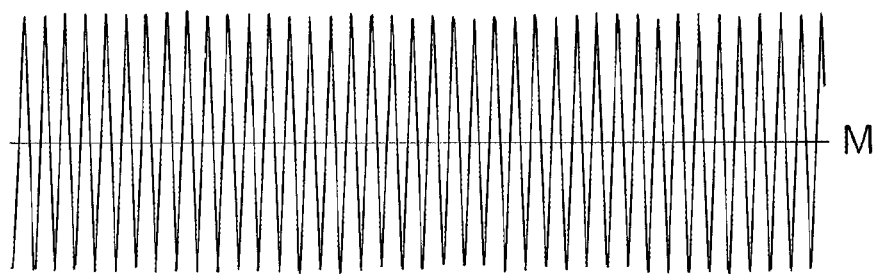
FIG. 4 is an enlarged view of a rectangular part b in FIG. 3.

Setting of the maximum allowable amount and minimum allowable amount of the variation in end surface gap d is described in more detail. FIGS. 2 to 4 are graphs illustrating a measurement result of the end surface gap d during the fatigue test in an intermittent operation mode. The vertical axes represent a detection value ($\mu$m) of the end surface gap d, and the horizontal axes represent time. Also, FIG. 3 is an enlarged view where an aspect ratio of a rectangular part a in FIG. 2 is changed, and FIG. 4 is an enlarged view where an aspect ratio of a rectangular part b in FIG. 3 is changed.

As illustrated in FIG. 2, regarding the end surface gap d, when the test piece S is excited, a value of the end surface gap d measured by the displacement meter 21 is largely fluctuated, and when the excitation is paused, a fluctuation range of the end surface gap d is small.

A reference end surface gap di serving as a reference for obtaining the variation in end surface gap d is determined by measurement before attaching the test piece S to the horn 12 and starting the excitation. The reference end surface gap di is the distance between the displacement meter 21 and the end surface of the test piece S before exciting the test piece S. Once the test piece S is excited, the value of the end surface gap d is fluctuated by the oscillation as indicated by a waveform in FIG. 4. For this reason, the center position M of the wave height in each period of the detected waveform by the displacement meter 21 is set as an end surface position of the test piece S to obtain the end surface gap d that is the distance from the displacement meter 21 to the end surface of the test piece S. Note that FIGS. 2 and 3 illustrate the outer shape of a collection of the waveforms because a period of the waveforms is extremely short as compared with the scales of the horizontal axes.

As illustrated in FIG. 3, the above-described maximum allowable amount $\Delta$dmax of the variation in end surface gap d is a displacement amount of the test piece S corresponding to the maximum change of a temperature rise inside the test piece by the excitation, and the difference between the reference end surface gap di and an end surface gap d obtained as a distance to the center position M of the wave height of a detected waveform by the displacement meter 21 at the time is $\Delta$d. When the test piece S is excited, heat generated in the test piece S elongates the test piece S, and therefore the value of the end surface gap d is shifted with time in a direction of becoming smaller (shorter) than a value of the reference end surface gap di (see FIGS. 2 and 3).

Also, as illustrated in FIG. 3, the minimum allowable amount $\Delta$dmin of the variation in end surface gap d is a displacement amount of the test piece S by which it can be determined that pausing the excitation decreases the temperature inside the test piece to a level where the excitation can be restarted, and the difference $\Delta$d between the reference end surface gap di and an end surface gap d obtained as a distance to the center position M of the wave height of a detected waveform by the displacement meter 21 at the time. When the excitation applied to the test piece S is paused to decrease the internal temperature of the test piece S, the elongation caused by the heat generated in the test piece S attempts to recover, and therefore the value of the end surface gap d is shifted with time in a direction of becoming larger (longer) than the value of the end surface gap d at the time when the test piece S is excited (see FIG. 2). That is, the minimum allowable amount $\Delta$dmin of the variation in end surface gap d is a displacement amount of the test piece S making it possible to determine that the heat generation of the test piece S is suppressed to bring the elongation of the test pieces S close to the state before the excitation.

In the ultrasonic fatigue testing machine, the internal temperature estimation part 31 obtains the variation in internal temperature of the test piece S using the linear expansion coefficient. Accordingly, the allowable range setting part 32 also calculates the maximum allowable amount Δdmax and minimum allowable amount Δdmin of the displacement amount from temperatures at which excitation should be paused and can be restarted, which are inputted by an operator using the input part 36, and the linear expansion coefficient.

Description is given with reference to FIG. 1 again. When the test piece S is excited, the determination part 33 determines whether or not the variation Δd that is the difference between the reference end surface gap di and the end surface gap d is larger than the maximum allowable amount Δdmax set in the allowable range setting part 32. Also, when the excitation applied to the test piece S is paused, the determination part 33 determines whether or not the variation Δd that is the difference between the reference end surface gap di and the end surface gap d is smaller than the minimum allowable amount Δdmin set in the allowable range setting part 32. On the basis of a result of the determination in the determination part 33, the control part 30 controls on/off of a signal output from the oscillator 15 to the ultrasonic transducer 11.

Figure 5:
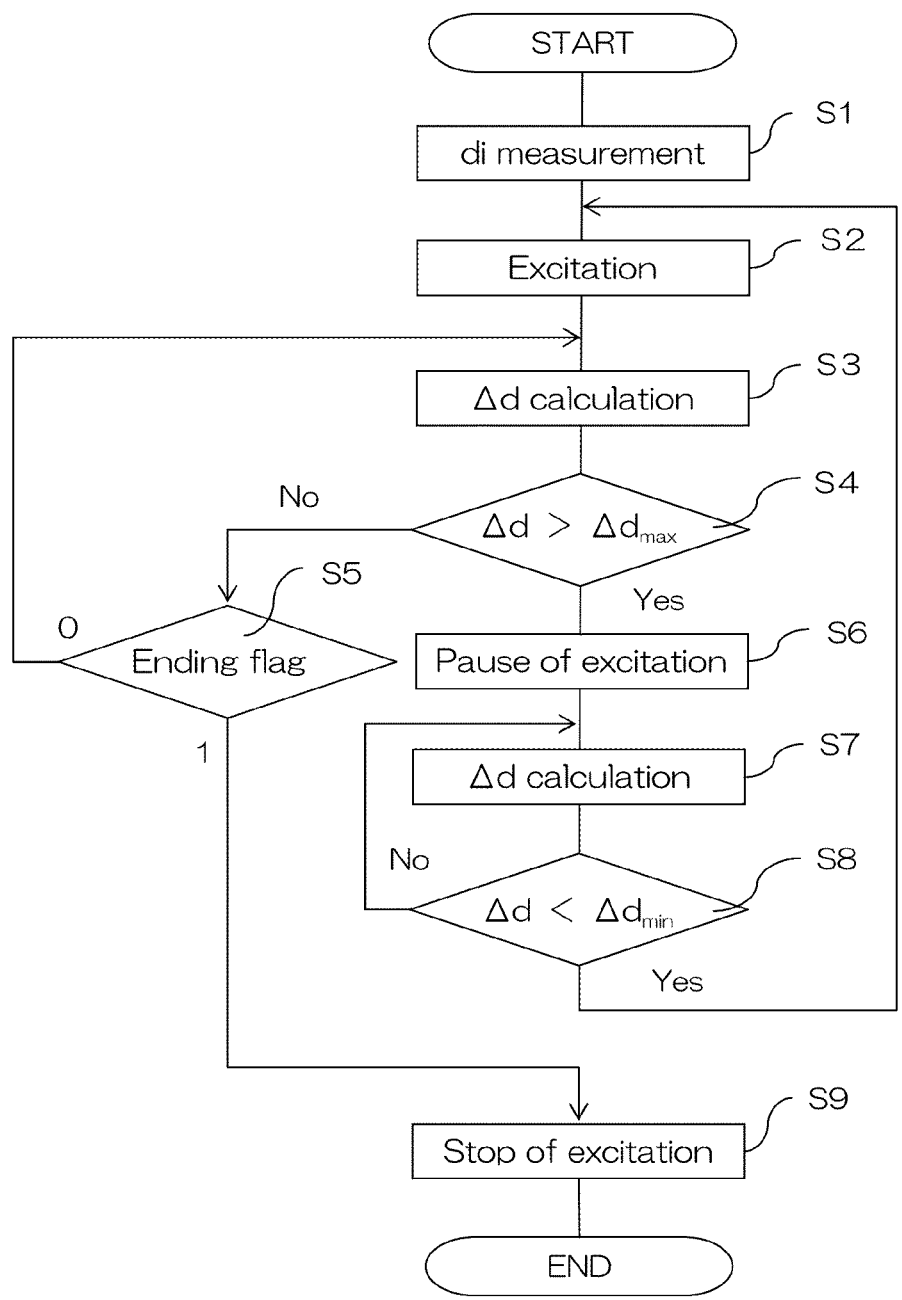
FIG. 5 is a flowchart illustrating an intermittent operation procedure in the ultrasonic fatigue testing machine of this invention.

Operation at the time of performing the ultrasonic fatigue test in the intermittent operation mode that suppresses a rise in temperature inside the test pieces while repeating excitation applied to the test piece S and a pause of the excitation in the ultrasonic fatigue testing machine having such a configuration is described. FIG. 5 is a flowchart illustrating an intermittent operation procedure in the ultrasonic fatigue testing machine of this invention.

When performing the ultrasonic fatigue test in the intermittent operation mode, first, before exciting the test piece S, the reference end surface gap di serving as a reference value of the distance between the displacement meter 21 and the end surface of the test piece S is measured (Step S1). After that, drive voltage for the ultrasonic transducer 11, which corresponds to a test frequency set in the control part 30, is outputted from the oscillator 15, and the test piece S is excited (Step S2).

During the test, the end surface gap d is continuously measured by the displacement meter 21. Note that as described above, the end surface gap d when doing this is the distance from the displacement meter 21 to the end surface of the test piece S with the center position M of the wave height in a detected waveform by the displacement meter 21 being set as the end surface position of the test piece S. Further, the difference between the reference end surface gap di measured before exciting the test piece S and the end surface gap d is calculated as the variation Δd (Step S3).

The variation Δd calculated in Step S3 is compared with the maximum allowable amount Δdmax (Step S4). In the case where the variation Δd is smaller than the maximum allowable amount Δdmax, and in the case where a signal for ending the test is not inputted, i.e., an ending flag=0 (Step S5), the excitation is continued. Subsequently, the calculation of the variation Δd with respect to a measured value of the end surface gap d inputted one after another, and the determination whether or not the variation Δd is smaller than the maximum allowable amount Δdmax are repetitively performed (Steps S3 and S4). Note that the signal for ending the test refers to a signal generated when the total time of a preset excitation time has just passed with a timer or the like being used or a detection signal at the time of detecting the breakage of the test piece S.

Further, in Step S5, in the case where the signal for ending the test is inputted to turn the ending flag to 1, the signal output from the oscillator 15 to the ultrasonic transducer 11 is turned off by a command from the control part 30 to stop the excitation (Step S9), and then the test is ended.

In the case where the variation Δd is larger than the maximum allowable amount Δdmax (Step S4), the signal output from the oscillator 15 to the ultrasonic transducer 11 is turned off by the command from the control part 30 to pause the excitation (Step S6). Even during the pause of the excitation, the variation Δd that is the difference between the reference end surface gap di and the end surface gap d is calculated (Step S7), and the variation Δd calculated at this time is compared with the minimum allowable amount Δdmin (Step S8). In the case where the variation Δd is larger than the minimum allowable amount Δdmin, the calculation of the variation Δd with respect to a measured value of the end surface gap d inputted one after another, and the comparison between the variation Δd and the minimum allowable amount Δdmin are repetitively performed while keeping the excitation pausing state (Steps S7 and S8).

In the case where the variation Δd is smaller than the minimum allowable amount Δdmin (Step S8), the signal output from the oscillator 15 to the ultrasonic transducer 11 is turned on by a command from the control part 30 to restart the excitation (Step S2). The above-described respective processing steps in Step S4 and S8 are performed in the determination part 33 of the control part 30. In this embodiment, such functions of the determination part 33 make it possible to automatically adjust an excitation time and a pause time during the test.

In this embodiment, during the test, by pausing the excitation at timing just after the calculated variation Δd has exceeded the maximum allowable amount Δdmax, the internal temperature of the test piece S can be prevented from exceeding an allowable temperature of a material of the test piece S in the fatigue test. Also, after pausing the excitation once, the excitation is restarted at timing when the variation Δd has just become smaller than the minimum allowable amount Δdmin, and therefore it is not necessary to take an unnecessarily long cooling time for the test piece S. That is, since at appropriate timings, excitation applied to the test piece S, and a pause of the excitation can be performed, a test time necessary for the ultrasonic fatigue test can be shortened.

In addition, the above-described embodiment is adapted to, in Step S8, in the case where the variation Δd is smaller than the minimum allowable amount Δdmin, return to Step S2, but may be adapted to return to Step S1. That is, just before each excitation cycle (one continuous excitation time), by measuring the distance from the displacement meter 21 to the end surface of the test piece S, and setting a measured value as the reference end surface gap di, a displacement amount due to plastic deformation caused by stress having been received by the test piece S can be removed from a variation Δd caused by excitation in the next excitation cycle. This makes it possible to further accurately estimate the amount of temperature rise of the test piece S.

REFERENCE SIGNS LIST

10 Ultrasonic wave generation part
11 Ultrasonic transducer
12 Horn
13 Oscillation part
15 Oscillator
20 Displacement measurement part
21 Displacement meter
22 Converter
30 Control part 31 Internal temperature estimation part
32 Allowable range setting part
33 Determination part
36 Input part
37 Display part
S Test piece

The invention claimed is:

1. An ultrasonic fatigue testing machine comprising:
an oscillator that outputs an electrical signal adapted to generate a high frequency wave;
an ultrasonic transducer that receives the electrical signal from the oscillator to oscillate;
a horn of which a fore end is attached with a test piece, the horn amplifying ultrasonic oscillation from the ultrasonic transducer to transmit the amplified ultrasonic oscillation to the test piece; and
a displacement meter that is arranged in a position away, by a predetermined distance, from an end surface of a free end of the test piece on a side opposite to an end part fixed to the horn, and measures a distance to the end surface of the test piece, and
performing a fatigue test in an intermittent operation mode that repeats excitation applied to the test piece and a pause, the ultrasonic fatigue testing machine including
a control part that has an internal temperature estimation part that, from a variation in the distance that is measured by the displacement meter and from the displacement meter to the end surface of the test piece, estimates internal temperature of the test piece, the internal temperature being due to internal heat generation of a material, the internal heat generation being caused by the ultrasonic oscillation, and on a basis of the internal temperature of the test piece, the internal temperature being estimated by the internal temperature estimation part, controls a start and a stop of the signal output from the oscillator.

2. The ultrasonic fatigue testing machine according to claim 1, wherein
the internal temperature estimation part estimates the internal temperature of the test piece with use of a linear expansion coefficient of the material of the test piece.

3. The ultrasonic fatigue testing machine according to claim 1, wherein
the control part has:
an allowable range setting part that sets a maximum allowable amount and a minimum allowable amount of the variation corresponding to a rise in the internal temperature of the test piece, the rise being allowable during the test; and
a determination part that when the test piece is excited, determines whether or not the variation is larger than the maximum allowable amount, and when the excitation applied to the test piece is paused, determines whether or not the variation is smaller than the minimum allowable amount, and
in a case where when the test piece is excited, the determination part determines that the variation is larger than the maximum allowable amount, pauses the signal output from the oscillator, and in a case where when the excitation applied to the test piece is paused, the determination part determines that the variation is smaller than the minimum allowable amount, starts the signal output from the oscillator.

4. An ultrasonic fatigue testing method that performs a fatigue test in an intermittent operation mode that repeats excitation applied to a test piece and a pause in an ultrasonic fatigue testing machine comprising: an oscillator that outputs an electrical signal adapted to generate a high frequency wave; an ultrasonic transducer that receives the electrical signal from the oscillator to oscillate; a horn of which a fore end is attached with a test piece, the horn amplifying ultrasonic oscillation from the ultrasonic transducer to transmit the amplified ultrasonic oscillation to the test piece; and a displacement meter that is arranged in a position away, by a predetermined distance, from an end surface of a free end of the test piece on a side opposite to an end part fixed to the horn, and measures a distance to the end surface of the test piece,
the ultrasonic fatigue testing method comprising:
an internal temperature estimation step of, from a variation in the distance that is measured by the displacement meter and from the displacement meter to the end surface of the test piece, estimating internal temperature of the test piece, the internal temperature being due to internal heat generation of a material, the internal heat generation being caused by the ultrasonic oscillation;
an allowable range step of setting a maximum allowable amount and a minimum allowable amount of the variation corresponding to a rise in the internal temperature of the test piece, the rise being allowable during the test; and
a determination step of, when the test piece is excited, determining whether or not the variation is larger than the maximum allowable amount, and when the excitation applied to the test piece is paused, determining whether or not the variation is smaller than the minimum allowable amount, and
in a case where when the test piece is excited, it is determined in the determination step that the variation is larger than the maximum allowable amount, pausing the signal output from the oscillator, and in a case where when the excitation applied to the test piece is paused, it is determined in the determination step that the variation is smaller than the minimum allowable amount, starting the signal output from the oscillator.

* * * * *